United States Patent [19]

Allen et al.

[11] Patent Number: 4,778,656

[45] Date of Patent: Oct. 18, 1988

[54] METHOD FOR ENHANCING IONIZING RADIATION

[75] Inventors: Richard B. Allen, Dalton; Roger W. Avakian, Pittsfield, both of Mass.

[73] Assignee: General Electric Company, Pittsfield, Mass.

[21] Appl. No.: 935,623

[22] Filed: Nov. 24, 1986

Related U.S. Application Data

[63] Continuation of Ser. No. 579,102, Feb. 10, 1984, abandoned.

[51] Int. Cl.$^4$ .......................... A61L 2/08; A61L 2/10; A61L 2/12
[52] U.S. Cl. ........................................ 422/20; 422/21; 422/22; 522/111; 525/439
[58] Field of Search .................... 525/439; 422/20, 21, 422/22; 522/111

[56] References Cited

U.S. PATENT DOCUMENTS

| | | | |
|---|---|---|---|
| 3,737,409 | 6/1973 | Fox | 528/174 |
| 4,124,652 | 11/1978 | Quinn . | |
| 4,125,572 | 11/1978 | Scott . | |
| 4,188,314 | 2/1980 | Fox . | |
| 4,391,954 | 7/1983 | Scott . | |
| 4,439,598 | 3/1984 | Sublett | 528/295.3 |
| 4,525,531 | 6/1985 | Zubosky | 525/92 |
| 4,616,064 | 10/1986 | Zubosky | 525/92 |
| 4,624,972 | 11/1986 | Nace | 523/136 |

*Primary Examiner*—Patricia Short
*Attorney, Agent, or Firm*—Hedman, Gibson, Costigan & Hoare

[57] ABSTRACT

The tendency of polymers which are normally transparent after molding to undergo yellowing upon exposure to ionizing radiation is reduced by blending them with another polymer that has the effect of improving the ionizing radiation resistance over and above a mere dilution effect. The blends are moldable into medical products that can be sterilized repeatedly with little or no yellowing.

1 Claim, No Drawings

METHOD FOR ENHANCING IONIZING RADIATION

This is a continuation of application Ser. No. 579,102, filed Feb. 10, 1984, now abandoned.

BACKGROUND OF THE INVENTION

Polymers which can be fabricated into transparent plastic articles, for example, aromatic polycarbonate resins and blends, are sometimes used in products for the medical field. These products include blood oxygenators, anesthesia canisters, intravenous connectors and accessories, pulsatile balloon pumps, and blood centrifuge banks. Such articles are frequently sterilized, typically by heating in an autoclave, or by contacting with ethylene oxide, or by exposure to ionizing radiation, e.g., gamma radiation or electron beam radiation. Each of these techniques has certain shortcomings, however. Autoclaves are often undesirable because of the thermal instability of many polymers, including polycarbonates and polyarylates, the relatively high energy requirements of the technique, and the residual wetness of the treated article which must first be dried before use.

The utilization of ethylene oxide is often objectionable because of its toxicity, instability and the environmental concerns associated with its disposal.

Sterilization by ionizing radiation is a useful alternative, being an essentially dry process which can be conducted at low temperatures and which is relatively inexpensive. The use of ionizing radiation when applied to articles made of polycarbonate and polyarylate resins in particular usually results, however, in the formation of a yellow coloration in the normally optically clear polymer. This can be regarded as unsightly, and to counteract the effect coloring agents have often been incorporated into the polymer to mask the yellow color which forms with one considered more esthetically acceptable, for instance, a bluish tinge.

SUMMARY OF THE INVENTION

The discovery has now been made of a method for increasing the ionizing radiation resistance of polymers which are normally prone to undergoing yellowing upon repeated or prolonged exposure to such radiation. The method comprises including a second polymer which forms a compatible blend with the first polymer and has the effect of stabilizing it against yellowing.

DETAILED DESCRIPTION OF THE INVENTION

The method of the invention generally involves bringing together, by way of admixing, at least two polymers which, in most cases, will be a homopolymer or copolymer containing aromatic carbonate units or a wholly aromatic polyester (polyarylate) and a homopolymer or copolymer containing other types of ester units, although other polymer combinations are possible as will be seen below. By way of illustration, polymers which are normally susceptible to ionizing radiation-caused yellowing include aromatic (homo) polycarbonates, poly (ester-carbonates), poly(sulfone-carbonates) and polyarylates, to mention those of chief interest in this disclosure. The ionizing radiation resistance of such polymers can be increased by admixture with a second polymer selected from among, for instance, polyester homopolymers, especially those based on the reaction of aliphatic or cycloaliphatic polyols with aromatic or cycloaliphatic dicarboxylic acids, copolyesters and the like.

The particular pairing in a given case will depend on whether a noticeable improvement in the ionizing radiation resistance and a concomitant reduction in the tendency to undergo yellowing are achieved. For instance, as a bare minimum requirement it is essential that the first and second polymers be of different specific classes, the observation having been made that no appreciable benefit is obtained if, for instance, a poly (sulfone-carbonate) is paired with another poly(sulfone-carbonate), a poly(aromatic carbonate) homopolymer paired with another poly(aromatic carbonate) homopolymer, a poly(ester-carbonate) is paired with another poly (ester-carbonate), and so forth. Below are listed various polymer combinations, or pairings, which are preferred and suggested for use in the practice of the invention:

| FIRST POLYMER | SECOND POLYMER |
| --- | --- |
| Polycarbonate homopolymer | (a) Polyester homopolymer |
|  | (b) Copolyester |
|  | (c) Poly(sulfone-carbonate) |
| Poly(ester-carbonate) | (a) Polyester homopolymer |
|  | (b) Copolyester |
|  | (c) Poly(sulfone-carbonate) |
| Polyarylate | (a) Polyester homopolymer |
|  | (b) Copolyester |

These various polymers and copolymers are described in greater detail below.

Polycarbonate homopolymers useful in this invention are especially aromatic polycarbonates. These can be made by those skilled in the art or obtained from various commercial sources. They may be prepared by reacting dihydric phenol with a carbonate precursor, such as phosgene, a haloformate or a carbonate ester. Typically, they will have recurring structural units of the formula:

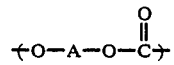

wherein A is a divalent aromatic radical of the dihydric phenol employed in the polymer producing reaction. Preferably, the aromatic carbonate polymers have an intrinsic viscosity ranging from 0.30 to 1.0 dl./g. (measured in methylene chloride at 25° C.) By dihydric phenols is meant mononuclear or polynuclear aromatic compounds containing two hydroxy radicals, each of which is attached to a carbon atom of an aromatic nucleus. Typical dihydric phenols include 2,2-bis-(4-hydroxy-phenyl)propane; 2-2-bis-(3,5-dimethyl-4-hydroxyphenyl)propane, 4,4'-dihydroxydiphenyl ether, bis(2-hydroxyphenyl)methane, mixtures thereof and the like. The preferred aromatic carbonte polymer is a homopolymer derived from 2,2-bis(4-hydroxyphenyl)-propane(bisphenol-A).

Poly(ester-carbonates) for use in the invention are known and can be obtained commercially. Generally, they are copolyesters comprising recurring carbonate groups:

carboxylate groups:

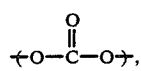

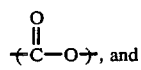

aromatic carbocyclic groups in the linear polymer chain, in which at least some of the carboxylate groups and at least some of the carbonate groups are bonded directly to ring carbon atoms of the aromatic carbocyclic groups. These poly(ester-carbonate) copolymers, in general, are prepared by reacting a difunctional carboxylic acid, such as phthalic acid, isophthalic acid, terephthalic acid, homophthalic acid, o-, m-, and p-phenylenediacetic acid, the polynuclear aromatic acids, such as diphenic acid, 1,4-naphthalic acid, mixtures of any of the foregoing, and the like, with a dihydric phenol and a carbonate precursor, of the types described above. A particularly useful polyester carbonate is derived from bisphenol-A, isophthalic acid, terephthalic acid, or a mixture of isophthalic acid and terephthalic acid, or the reactive derivatives of these acids such as terephthaloyl dichloride, isophthaloyl dichloride, or a mixture thereof, and phosgene. The molar proportions of dihydroxy diaryl units to benzenedicarboxylate units to carbonate units can range from 1:0.2–1.00:0.80–0.00 and the molar range of terephthalate units to isophthalate units can range from 99:1 to 1:99 in this preferred family of resins. When the molar proportion of carbonate units is 0, the resin is a wholly aromatic polyester. See Robeson, U.S. Pat. No. 4,324,869.

The aromatic dihydric phenol sulfone resins used in this invention are a family of resins which can be made by those skilled in this art. For example, homopolymers of dihydric phenol, and a dihydroxydiphenyl sulfone and a carbonate precursor can be prepared, as well as copolymers of a dihydric phenol and a carbonate precursor can be made according to the description in Schnell, et al., U.S. Pat. No. 3,271,367. A preferred material is made by polymerizing bis-(3,5-dimethyl-4-hydroxy phenyl) sulfone, alone, or especially in combination with bisphenol-A with phosgene or a phosgene precursor, in accordance with the description in Fox, U.S. Pat. No. 3,737,409. Especially preferred is a copolymer made by reacting 1–99, preferably 40–99 wt. percent of the sulfone, 99 to 1, preferably 60 to 1 wt. percent of the bisphenol with phosgene.

Polyesters suitable for use herein are derived from an aliphatic, aliphatic ether or cycloaliphatic diol, or mixtures thereof, preferably containing from about 2 to about 10 carbon atoms, and one or more aromatic or cycloaliphatic dicarboxylic acids. Preferred polyesters are derived from an aliphatic diol and an aromatic dicarboxylic acid having repeating units of the following general formula:

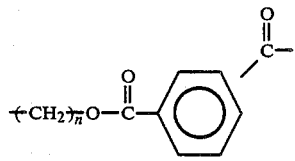

wherein n is an integer of from 2 to 4. The most preferred polyester is poly(ethylene terephthalate).

Also contemplated herein are the above polyesters with additional amounts of polyols and/or acids in the amounts of from 0.5 to 50 wt. percent based on the total composition. The acids can be aliphatic or cycloaliphatic with the number of carbon atoms ranging from 2 to 20. Likewise, the glycols can be cycloaliphatic or aliphatic with the number of carbon atoms covering the same range. Polyalkylene ether glycols can also be used where the alkylene portion has from 2 to 10 carbon atoms and the entire glycol portion varies in molecular weight from 100 to 10,000. All such polyesters can be made following the teachings of, for example, U.S. Pat. Nos. 2,465,319 and 3,047,539.

The polyesters which are derived from a cycloaliphatic diol and an aromatic dicarboxylic acid are prepared, for example, by condensing either the cis- or trans-isomer (or mixtures thereof) of, for example, 1,4-cyclohexanedimethanol with an aromatic dicarboxylic acid so as to produce a polyester having recurring units of the following formula:

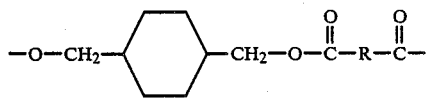

wherein the cyclohexane ring is selected from the cis- and trans-isomers thereof and R represents an aryl or cycloaliphatic radical containing 6 to 20 carbon atoms and which is the decarboxylated residue derived from an aromatic dicarboxylic acid.

Examples of aromatic dicarboxylic acids represented by the decarboxylated residue R are isophthalic or terephthalic acid, 1,2-di(p-carboxyphenyl)ethane, 4,4'-dicarboxydiphenyl ether, etc., and mixtures of these. Acids containing fused rings can also be present, such as in 1,4- or 1,5-naphthalenedicarboxylic acids. Also contemplated are cycloaliphatic diacids, such as cyclohexane dicarboxylic acid. The preferred dicarboxylic acids are terephthalic acid or a mixture of terephthalic and isophthalic acids.

Another preferred polyester may be derived from the reaction of either the cis- or trans-isomer (or a mixture thereof) of 1,4-cyclohexanedimethanol with a mixture of isophthalic and terephthalic acids. Such a polyester would have repeating units of the formula:

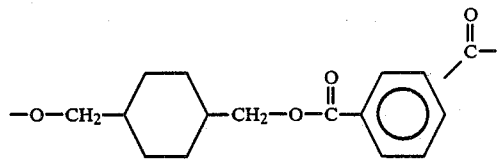

Still another preferred polyester is a copolyester derived from a cyclohexane dimethanol, an alkylene glycol and an aromatic dicarboxylic acid. These copolyesters are prepared by condensing either the cis- or trans-isomer (or mixtures thereof) of, for example, 1,4-cyclohexane-dimethanol and an alkylene glycol with an aromatic dicarboxylic acid so as to produce a copolyester having units of the following formula:

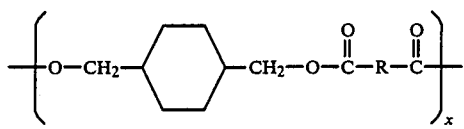

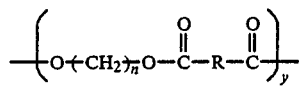

wherein the cyclohexane ring is selected from the cis- and trans-isomers thereof, R is as previously defined, n is an integer of 2 to 10, the x units comprise from about 1 to about 99 percent by weight, and the y units comprise from about 99 to about 1 percent by weight.

Such a preferred copolyester may be derived from the reaction of either the cis- or trans-isomer (or mixtures thereof) of 1,4-cyclohexanedimethanol and ethylene glycol with terephthalic acid in a molar ratio of 80:20:100. These copolyesters have repeating units of the following formula:

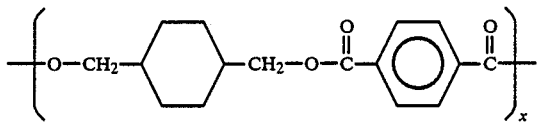

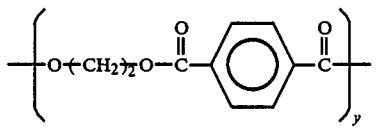

wherein x and y are as previously defined.

The polyesters described herein are either commercially available or they can be produced by methods known in the art, including those set forth in U.S. Pat. No. 2,901,466.

The polyesters employed in the practice of this invention will usually have an intrinsic viscosity of from about 0.4 to about 2.0 dl./g., as measured in a 60:40 phenol:tetrachloroethane mixture, or similar solvent at 23°–30° C.

The relative amounts of the polymers can and usually do vary widely in the blend, with particular amounts depending on specific requirements and the nature of the polymers being employed. Proportions can range, for example, between 99:1 and 1:99, based on 100 parts by weight of the two polymers together. Best amounts in a given instance will be readily determinable by those skilled in the art.

Preparation of admixtures of the polymers may be carried out in any convenient manner. In the usual case, finely divided dry powders of the polymers are simply blended together on a mechanical mixer and the blend is compounded by passage through an extruder at an elevated temperature above the softening points of the polymeric constituents. Alternatively, however, the polymers may be dissolved in a mutual solvent from which they are subsequently recovered in blended form by evaporation, distillation or precipitation.

The resulting polymer blend can be further modified, if desired, by incorporation of standard amounts of conventional additives to upgrade other physical or chemical properties. The additive or additives can be selected from among, by way of illustration, plasticizers, thermal stabilizers, antioxidants, flame retardants, lubricants, fillers, reinforcing agents, and so on. These are most conveniently added during the initial stages of polymer blend formation.

The blends may be subsequently processed into molded articles of various shapes and sizes and they are especially useful in medical products such as those described above. These may be subjected to the rigorous conditions required for sterilization, without any or only small losses in the optical clarity.

DESCRIPTION OF THE SPECIFIC EMBODIMENTS

The invention is further illustrated in the following examples, which are presented to show best or preferred embodiments and not meant to limit the scope of the invention.

EXAMPLES 1–17

The polymer blends noted below were prepared by forming an admixture, extruding at a temperature of from 500° to 600° F. and injection molding into test pieces at a temperature of from 500° to 580° F. The same was done for several of the polymers separately, which are identified as controls. Color change was evaluated using Cobalt-60 as the gamma radiation source, with dosages (in Mrads) as shown. The yellowness index (YI) was measured in accordance with the ASTM procedure. The slopes were calculated from a plot of the delta yellowness index versus the radiation dose. Lower slope values for the blends, in relation to the controls, is indicative of less yellowing. The formulations used and the results obtained are set forth in TABLE 1:

TABLE 1

| Ex. | Base Resin | Additive | Additive Amt., wt. % | After Irradiation Dose | ΔYI | Slope |
|---|---|---|---|---|---|---|
| A* | Poly(bisphenol-A carbonate)[a] | None | 0 | 5.7 | 42.34 | 7.42 |
| 1 | Same | Poly(carbonate-sulfone)[b] | 20 | 5.7 | 21.49 | 3.77 |
| 2 | Same | Poly(carbonate-sulfone)[b] | 50 | 5.7 | 19.06 | 3.34 |
| 3 | Same | Poly(carbonate-sulfone)[b] | 75 | 5.7 | 13.70 | 2.40 |
| B* | None | Poly(carbonate-sulfone)[b] | 100 | 5.2 | 7.1 | 1.36 |
| 4 | Poly(bisphenol A carbonate) | Polyethylene terephthalate | 23 | 5.0 | 22 | 4.4 |
| 5 | Same | Polyethylene terephthalate | 40 | 5.0 | 21 | 4.2 |
| C* | None | Polyethylene | 100 | 5.0 | 2 | 0.4 |

TABLE 1-continued

| Ex. | Base Resin | Additive | Additive Amt., wt. % | After Irradiation Dose | ΔYI | Slope |
|---|---|---|---|---|---|---|
| 6 | Poly(bisphenol A carbonate) | Copolyester of cyclohexane dimethanol, ethylene glycol and terephthalic acid terephthalate | 20 | 5.0 | 13 | 2.6 |
| 7 | Same | Same copolyester | 40 | 5.0 | 8 | 1.6 |
| 8 | Same | Same copolyester | 60 | 5.0 | 5.5 | 1.1 |
| 9 | Same | Same copolyester | 80 | 5.0 | 4.0 | 0.8 |
| D* | None | Same copolyester | 100 | 5.0 | 10.0 | 2.0 |
| 10 | Poly(bisphenol-A carbonate) | Polyester of 1,4-cyclohexanedimethanol and 1,4-cyclohexane dicarboxylic acid[c] | 50 | 5.8 | 9.64 | 1.66 |
| 11 | Same | Hydroxy-terminated polyester of ethylene glycol, phthalic acid, and branching agent[d] | 10 | 2.5 | 6.90 | 2.76 |
| 12 | Same | Polyester derived from ethylene, and butylene glycol and adipic acid[e] | 10 | 2.5 | 8.68 | 3.47 |
| 13 | Same | Copolyester: 85 mole % terephthalate, 15 mole % isophthalate and 1,4-cyclohexane dimethanol[f] | 10 | 5.0 | 14.1 | 2.82 |
| 14 | Same | Copolyester[f] | 20 | 5.0 | 11.1 | 2.22 |
| 15 | Same | Copolyester[f] | 30 | 5.0 | 9.4 | 1.88 |
| 16 | Same | Copolyester[f] | 40 | 5.0 | 7.6 | 1.52 |
| 17 | Same | Copolyester[f] | 50 | 5.0 | 8.0 | 1.60 |
| E* | None | Copolyester[f] | 100 | 5.0 | 7.0 | 1.40 |

*control experiment
[a]LEXAN ®, General Electric Co.
[b]Fox, U.S. Pat. No. 3,737,409, Example IV.
[c]PCCE, Eastman Kodak Co.
[d]ADMEX 433, Sherex Chemical Co., Inc.
[e]ADMEX SC 3636-70, Sherex
[f]KODAR, Eastman Kodak Co.

It should be noted that some of these formulations may undergo darkening during high temperature processing and thus their use would probably be restricted to opaque or dark-colored articles.

EXAMPLE 18

The general procedure of Examples 1-17 was repeated, substituting for the second resin a copolyester comprising units derived from poly(tetramethyleneether)glycol (24 wt. %), 1,4-butanediol (16 wt. %), and neopentyl glycol (4 wt. %), and terephthalic acid (56 wt. %). A small amount of catalyst quenching aid, phosphorus acid, was included. The ratio of polycarbonate to copolyester was 1:1. After exposure to a gamma radiation source and comparison with unmodified polycarbonate exposed to a similar source, there was visually observed hardly any yellowing with the composition of this example. Unmodified polycarbonate yellowed significantly.

EXAMPLE 19

The general procedure of Examples 1-17 was repeated, and a small amount of a combination of tinting dyes and a small amount of a quenching aid, phosphorous acid, were also included. In addition to exposure to a gamma radiation source, some of the specimens were exposed to a source of electron beam radiation, which yellows unmodified polycarbonate significantly. The formulations employed and the results obtained are set forth in TABLE 2:

TABLE 2

| Example | 19 |
|---|---|
| Composition (parts by weight) | |
| Poly(bisphenol A carbonate)[a] | 50 |
| Copolyester: 85 mole % terephthalate, 15 mole % isophthalate and 1,4-cyclohexane dimethanol[b] | 50 |
| Mixed red and blue dyes | 0.00102 |
| Properties | Yellowness Index, YI |
| Gamma irradiated, dosage | |
| 0 | 0.97 |
| 1.5 megarads | 3.48 |
| 2.5 megarads | 4.85 |
| 5 megarads | 7.48 |
| Electron beam irradiated, dosage | |
| 0 | 1.5 |
| 1.5 megarads | 5.13 |
| 2.5 megarads | 6.96 |
| 3.0 megarads | 6.35 |

[a]LEXAN ®, General Electric Co.
[b]KODAR ®, Eastman Kodak Co.

The composition of Example 19 was color stabilized against both gamma radiation and electron beam radiation.

All of the above mentioned patents are incorporated herein by reference.

Other modifications and variations are possible in the light of the above disclosure. For example, if a polyarylate polymer comprising units derived from bisphenol A and terephthalic acid is substituted for the poly(bisphenol A carbonate) polymer in the composition of Example 19, a composition color stabilized against both gamma radiation and electron beam radiation will be obtained. It is to be understood, therefore, that changes may be made in the particular embodiments shown which are within the scope of the invention defined in the appended claims.

We claim:
1. In a method for sterilizing a transparent plastic article by ionizing radiation, the improvement which comprises utilizing as the transparent plastic article, an article which is made from a polymer composition.

* * * * *

UNITED STATES PATENT AND TRADEMARK OFFICE
CERTIFICATE OF CORRECTION

PATENT NO. : 4,778,656
DATED : October 18, 1988
INVENTOR(S) : Richard B. Allen and Roger W. Avakian It is certified that error appears in the above—identified patent and that said Letters Patent is hereby corrected as shown below:

In Claim 1, line 4, after the word "composition" add --comprising a bisphenol-A polycarbonate, and a copolyester of ethylene glycol, cyclohexane dimethanol and an aromatic acid--

Signed and Sealed this

Twenty-first Day of March, 1989

Attest:

DONALD J. QUIGG

Attesting Officer      Commissioner of Patents and Trademarks